US009629966B2

(12) United States Patent
Ji

(10) Patent No.: US 9,629,966 B2
(45) Date of Patent: Apr. 25, 2017

(54) INTERNAL DRY POWDER DELIVERY SYSTEM AND METHOD THEREOF

(71) Applicant: Xin Ji, San Jose, CA (US)

(72) Inventor: Xin Ji, San Jose, CA (US)

( * ) Notice: Subject to any disclaimer, the term of this patent is extended or adjusted under 35 U.S.C. 154(b) by 0 days.

(21) Appl. No.: 14/220,105

(22) Filed: Mar. 19, 2014

(65) Prior Publication Data

US 2014/0207097 A1 Jul. 24, 2014

Related U.S. Application Data

(60) Division of application No. 13/658,798, filed on Oct. 23, 2012, now Pat. No. 8,827,980, which is a (Continued)

(51) Int. Cl.

| | |
|---|---|
| ***A61M 13/00*** | (2006.01) |
| ***B05B 11/06*** | (2006.01) |
| ***A61M 11/00*** | (2006.01) |
| ***A61M 15/00*** | (2006.01) |
| *A61B 17/00* | (2006.01) |

(52) U.S. Cl.

CPC .......... *A61M 13/00* (2013.01); *A61M 11/007* (2014.02); *A61M 11/008* (2014.02); *A61M 15/0016* (2014.02); *B05B 11/062* (2013.01); *A61B 17/00491* (2013.01); *A61B 2017/00893* (2013.01); *A61M 2202/064* (2013.01)

(58) Field of Classification Search

CPC ...... A61M 2205/075; A61M 2202/064; A61M 15/0065; A61M 11/02; A61M 11/06; A61M 2011/008; A61M 5/2053; A61M 5/3015; A61M 2011/02; A61M 2011/06; A61M 2005/2053; A61M 2005/3015; A61M 2015/00–2015/0086; B05B 11/062; B05B 7/1431

See application file for complete search history.

(56) References Cited

U.S. PATENT DOCUMENTS 1,934,793 A * 11/1933 Crain .................... A61M 31/00 604/217
5,800,381 A * 9/1998 Ognier ................ A61M 13/003 600/560

(Continued)

*Primary Examiner* — Emily Schmidt
*Assistant Examiner* — William Carpenter
(74) *Attorney, Agent, or Firm* — Raymond Y. Chan; David and Raymond Patent Firm

(57) ABSTRACT

An internal dry powder delivery system through a working channel of an endoscopic cannula for directly applying the powder form medication to an internal tissue/organ site, includes an elongated tubular delivery channel and a powder supply device for producing pressurized gas mixing with the dry powder for feeding to form a mixture of dry powder and pressurized gas delivering to an internal tissue/organ site through the delivery channel via endoscopic cannula. It ensures a smooth powder release by preventing liquid from accumulation at the tip of the delivery channel and offers physicians a new powder form drug delivery method via endoscope. Also, it offers new minimal invasive application by directly and precisely applying the powder format drug to the internal sites of human gastrointestinal organ via endoscope to achieve hemostasis, anti-inflammation, anti-ulcer and anti-tumor treatment, etc.

10 Claims, 9 Drawing Sheets

Related U.S. Application Data continuation of application No. 12/932,582, filed on Feb. 28, 2011, which is a continuation-in-part of application No. 12/657,224, filed on Jan. 15, 2010, now Pat. No. 8,721,582.

(56) References Cited

U.S. PATENT DOCUMENTS

| | | | | |
|---|---|---|---|---|
| 5,951,531 | A * | 9/1999 | Ferdman | A61M 11/02 604/24 |
| 2003/0181917 | A1 * | 9/2003 | Gertner | A61M 35/003 606/82 |

* cited by examiner

INTERNAL DRY POWDER DELIVERY SYSTEM AND METHOD THEREOF

CROSS REFERENCE OF RELATED APPLICATION

This is a Divisional application that claims the benefit of priority under 35 U.S.C. §119 to a non-provisional application Ser. No. 13/658,798, filed Oct. 23, 2012, which is a Continuation application of a non-provisional application, application Ser. No. 12/932,582, filed Feb. 28, 2011, which is a Continuation-In-Part application of a non-provisional application, application Ser. No. 12/657,224, filed Jan. 15, 2010.

BACKGROUND OF THE PRESENT INVENTION

Field of Invention

The present invention relates to dry powder delivery system, and more particular to an internal dry powder delivery system and method thereof for delivering dry powder to reach internal operation site, especially during a minimally invasive surgery or other similar internal application for beings such as humans or animals.

Description of Related Arts

Generally, medications are in liquid form, capsule form, pill form, and powder form. The common difficulty for physicians is how to directly apply powdered medication to the internal tissue/organ site of a human or an animal such as human gastro-intestine.

Traditionally, the only application of powdered medications is to enclose the powder in a capsule made of a material that will not immediately dissolve or to compress the powder into the pill form. When the capsule or pill is consumed into the patient's stomach and intestine, the enclosure skin of the capsule will dissolve and the powder particles will be exposed and absorbed.

Conventionally, powder form medications can be applied by topical application during open surgery. It may normally be ingested as tablets or powder capsules. Tablets and powder capsules' strengths are often diluted by gastric and intestinal juice and could not offer precise delivery and dosage control to the target wound site. In turn, physicians can not accurately control the amount of medication reaching the designated site. Therefore, it cannot be used when physicians want to directly control the dosage and dryness status of the powder to apply the target wound sites of human gastro-intestine before contact with liquid in the digestive system.

The minimal invasive procedure via endoscope has been widely used for diagnosis and surgery. When using endoscope during inspection and surgery, physicians often need to apply medications to an internal tissue site. Via endoscope, physicians can inspect the internal organ/tissue and conduct surgical procedures inside of the human body. In general, endoscopes consist of gastro-intestinal endoscope, laparoscope, thoracoscope, hysteroscope, cytoscope, laryngoscope, and nasopharyngoscope etc. Besides for medical use, endoscopes can also be used to inspect mechanical or electrical problems in the industries such as automobile maintenance, mechanical setups, petroleum engineering, electrical facilities, aviator equipments, coal-gas passages, architectures, water pipe systems etc.

For example, laparoscope and gastro-intestinal endoscopes have a standard total length about 600 mm to 1700 mm depend on the application purpose. Besides the imaging system, the internal components include a narrow working channel, similar to that of an irrigation channel or a biopsy clamp, allowing physicians to conduct minimally invasive surgeries. Currently, the most common laparoscopic and gastro-intestinal scopes used by physicians for biopsy, have a diameter of 2.8 mm and 3.2 mm respectively to enable physicians to insert catheters or devices to conduct examination, electrical incision, suture, applying medication and hemostasis, etc.

Physicians often use laparoscope and gastro-intestinal endoscope during treatment and minimally invasive surgery to examine an internal site or to inject liquid medications. The long and narrow characteristics of the working channel often cause occlusion when injection medications which could present certain limitations. In current clinical settings, endoscope's irrigation or working channel could only delivery liquid form medications (soluble/insoluble solutions and gel), restricting any powder and particle form medications that could easily lose its effectiveness when it contacts water prior to blood. In addition, through the use of endoscopes physicians could often examine gastritis lesions including tumors or ulcers and thereby provide the appropriate topical medication directly to the site. Due to the length and the narrowness of most laparoscopes and endoscopes, particles often could not overcome the resistance presented between air pressure and the inner lining of the tube which could lead to tip occlusion. Also, gastro and intestinal juice/mucus could easily enter the working channel causing obstruction. The most common problems associated with delivering dry powder medication through the working channel of an endoscopic cannula include that dry powder particles often occlude because of resistance in the long and narrow cannula through the working channel of endoscope and excess liquid and pressurized air mixed with dry particles could cause occlusion at the tip of the delivery catheter. These common problems minimize physicians' ability to deliver powdered medications directly and precisely to the tissue/organ site of the human gastro-intestine via endoscope.

Recently, natural orifice transluminal endoscopic surgery was developed for minimally invasive surgical technique. The endoscope is inserted through natural orifices (such as mouth, anus and vagina) allowing for intra-abdominal diagnostic and therapeutic procedures without the need for abdominal incisions. Moreover, the endoscope can also be inserted into pre-existing orifices to access other body cavities (i.e. thoracic cavity and pelvic cavity). Hence a technique that utilizes the working channel of the endoscope as a vehicle to directly deliver medication to the internal target tissue/organ has great clinical implications in medicine.

The current invention specifically addresses these issues and provides physicians a new alternative to delivery particles/powder format medications directly to an internal site of gastrointestinal tract and body cavities via endoscope during minimally invasive surgeries for both diagnostic and therapeutic purposes.

SUMMARY OF THE PRESENT INVENTION

The present invention is advantageous in that it provides an internal dry powder delivery system which is capable of directly applying dry powder to internal tissue/organ site.

Another advantage of the present invention is to provide an internal dry powder delivery system via working channel of endoscopic cannula to overcome the difficulties when directly applying powdered medication to the tissue/organ site of human gastro-intestine through the narrow working channel of an endoscope.

Another advantage of the present invention is to provide a new dry powder-format drug delivery method and system thereof via working channel of endoscopic cannula, and its clinical applications, which overcome the most common problems associated with delivering dry powder medication through the working channel of an endoscopic cannula, including that dry powder particles often occlude because of resistance in the long and narrow cannula through the working channel of endoscope and excess liquid and pressurized air mixed with dry particles could cause occlusion at the tip of the delivery catheter, in which these common problems minimize physicians' ability to deliver powdered medications directly and precisely to the tissue/organ site of the human gastro-intestine via endoscope.

Another advantage of the present invention is to offer physicians an innovative powder medication delivery system and method thereof, a new diagnosis and treatment alternatives when performing a minimally invasive procedure, such as via endoscope.

Another advantage of the present invention is to offer physicians an innovative powder medication delivery system and method thereof, a new diagnosis and treatment alternatives when performing a minimally invasive procedure, such as via endoscope.

Another advantage of the present invention is to provide an innovative internal powder delivery system and method thereof which can directly reach the internal tissues in the internal cavities and deliver internal powder thereto.

Another advantage of the present invention is to offer physicians a new powder medication delivery system through the working channel of the endoscope, to directly reach the internal tissues in the gastrointestinal tract, abdominal, chest and pelvic cavity and deliver biomaterial for the purpose of tissue healing, sealing, anti-adhesion, fistula closure hemostasis etc.

Another advantage of the present invention is to provide a new powder form medication delivery method for physicians via endoscope. This method could be used with various purposes such as hemostatic, anti-flammation, tissue repair, mucosal protection, ulcer repair and antineoplastic treatment, etc.

Another advantage of the present invention is to provide a dry powder delivery system via the endoscope working channel that can be used to deliver biomaterials including nanomaterials, proteins, amino acids, minerals, trace elements, organic and non organic materials, polysaccharides, polymeric substances, fiber, microfiber, nutrient powder, adhesives, and etc.

Another advantage of the present invention is to provide an internal dry powder delivery system which enables physicians to directly apply the biocompatable polysaccharide hemostatic powder to the bleeding sites via endoscope during minimally invasive surgery to achieve hemostasis.

In order to accomplish the above advantages, the present invention provides an internal dry powder delivery system for delivering dry powder from outside to an internal operation site, comprising:

an elongated tubular delivery channel having a feeding opening at one end thereof, an emitting opening at a distal end thereof adapted for reaching a position adjacent to the internal operation site, a diameter 3.2 mm or less, and a length long enough for enabling the emitting opening reaching the internal operation site; and a powder supply device which is connected to the feeding opening of the delivery channel and comprises:

a gas-powder chamber a dry powder inlet for feeding in a predetermined amount of dry powder therein and a dry powder outlet communicating with the feeding opening of the delivery channel; and a pressurized gas feeder producing pressurized gas in the gas-powder chamber mixing with the dry powder therein to form a mixture of dry powder and pressurized gas for blowing into the delivery channel through the feeding opening thereof, thereby a continuous feeding of the pressurized gas and the mixture of dry powder and pressurized gas into the delivery channel from the gas-powder chamber substantially renders the mixture of dry powder and pressurized gas to deliver to the emitting opening of the delivery channel and spray onto the designated internal operation site.

The present invention also provides a method of delivering dry powder from outside to an internal operation site, comprising the steps of:

(a) extending a distal end of an elongated tubular delivery channel to a position adjacent to an internal operation site while the other end thereof remains outside;

(b) producing pressurized gas and mixing the pressurized gas with dry powder to form a mixture of dry powder and pressurized gas in a gas-powder chamber communicating with a feeding opening provided at the other end of the delivery channel; and (c) continuously feeding the pressurized gas and the mixture of dry powder and pressurized gas from the gas-powder chamber into the delivery channel via the feeding opening until a predetermined amount of the mixture of dry powder and pressurized gas spray out of an emitting opening provided at the distal end of the delivery channel for applying onto the internal operation site.

According to a preferred embodiment of the present invention, to prevent from powder occlusion in the catheter while inserting catheter into endoscope working channel to its designated position, a special feature of 'dual gas channels' was provided. One of the gas channels provides a 'maintaining gas flow' to ensure that the pressure inside the catheter is higher than the pressure inside the gastrointestinal tract or the thoracic/abdominal cavity where the catheter tip is located. This prevents from gas reflux from the gastrointestinal tract or thoracic/abdominal cavity into the catheter which may result in powder occlusion in the catheter. The working gas flow on the other hand delivers the dry powder to the designated site through the catheter.

According to a preferred embodiment of the present invention, the delivery channel can be inserted into a human or an animal body to reach a designated internal tissue operation site via a working channel of endoscopic cannula.

Additional advantages and features of the invention will become apparent from the description which follows, and may be realized by means of the instrumentalities and combinations particular point out in the appended claims.

DETAILED DESCRIPTION OF THE PREFERRED EMBODIMENT

Figure 1:
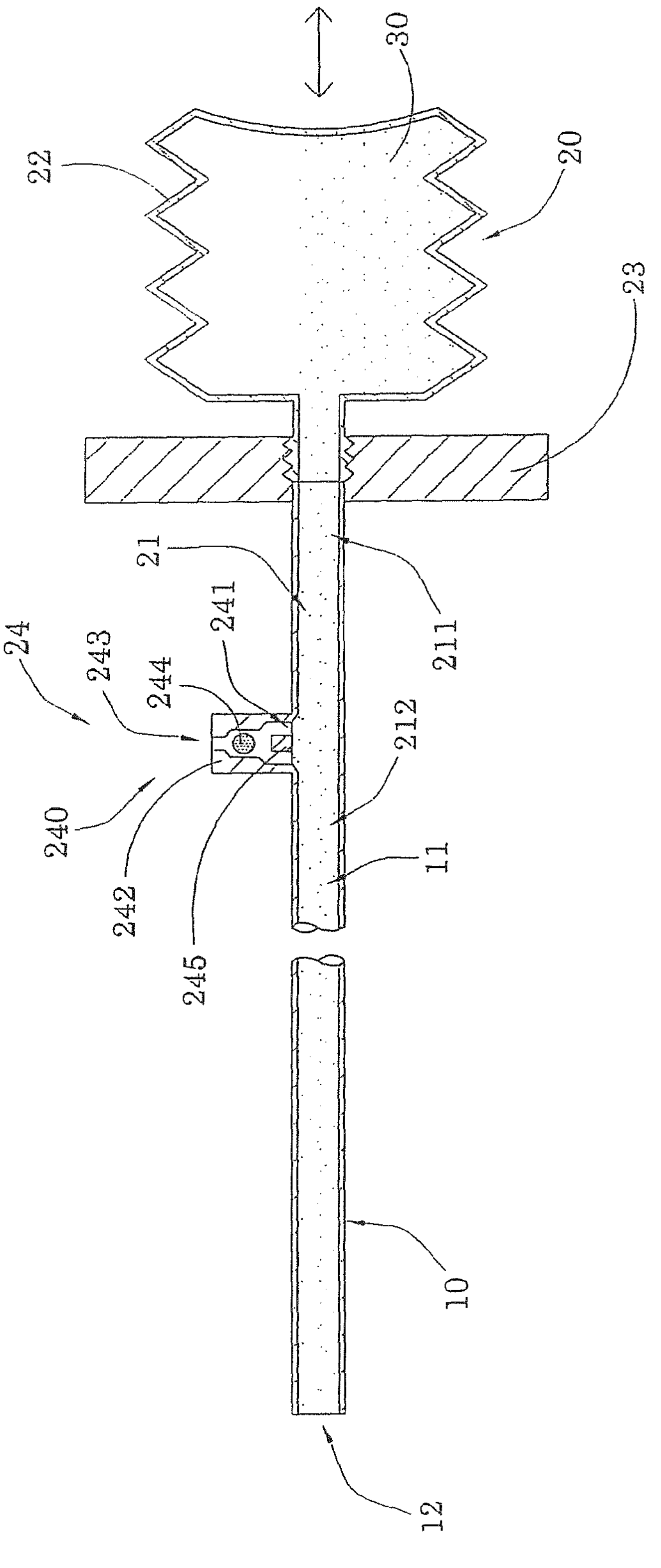
FIG. 1 is a sectional view of an internal dry powder delivery system according to a preferred embodiment of the present invention.

Referring to FIGS. 1 to 7, the present invention provides an internal dry powder delivery system and method thereof for delivering dry powder from outside to a designated internal operation site. According to a preferred embodiment, the present invention discloses a new dry powder medication delivery method via endoscope, and its clinical applications thereof, as an example to illustrate the configuration and improved features of the present invention. It is preferably aimed to, but not limited to, overcome the difficulties when directly applying powder medication to the internal operation (tissue/organ) site of human or animal such as human orgastro-intestine, organs, and etc. . . .

According to the preferred embodiment as illustrated in FIGS. 1-7, the present invention enables the delivering of dry powder medication through a working channel of an endoscopic cannula. In order to do so, the following problems must be overcome:

(i) Dry powder particles often occlude because of resistance in the long and narrow cannula through the working channel of endoscope.

(ii) Excess liquid and pressurized air mixed with dry particles could also cause occlusion at the tip of the delivery catheter.

These common problems minimize physicians' ability to deliver powder medications directly and precisely to the tissue/organ site of, for example, the human gastro-intestine via endoscope. To effectively address the above technical difficulties, the present invention provides an internal dry powder delivery system for delivering dry powder from outside to an internal operation site, which comprises an elongated tubular delivery channel 10 and a powder supply device 20.

The elongated tubular delivery channel 10 has a feeding opening 11 at one end thereof, an emitting opening 12 at a distal end thereof adapted for reaching a position adjacent to the internal operation site, a diameter preferably 3.2 mm or less, and a length long enough for enabling the emitting opening 12 reaching the internal operation site.

The powder supply device 20 which is connected to the feeding opening 11 of the delivery channel 10 comprises a gas-powder chamber 21 and a pressurized gas feeder 22.

The gas-powder chamber 21 has dry powder inlet 211 for feeding in a predetermined amount of dry powder therein and a dry powder outlet 212 communicating with the feeding opening 11 of the delivery channel 10.

The pressurized gas feeder 22 produces pressurized gas in the gas-powder chamber 21 mixing with the dry powder therein to form a mixture of dry powder and pressurized gas for blowing into the delivery channel 10 through the feeding opening 11 thereof. Thereby, a continuous feeding of the pressurized gas and the mixture of dry powder and pressurized gas into the delivery channel 10 from the gas powder chamber 21 substantially renders the mixture of dry powder and pressurized gas to deliver to the emitting opening 12 of the delivery channel 10 and spray onto the designated internal operation site.

By means of the above system, the procedures of delivering dry powder from outside to the internal operation site comprise the steps of:

(a) extending a distal end of the elongated tubular delivery channel 10 to a position adjacent to the internal operation site while the other end thereof remains outside;

(b) producing pressurized gas and mixing the pressurized gas with the dry powder to form a mixture of dry powder and pressurized gas in the gas-powder chamber 21 communicating with the feeding opening 11 of the delivery channel 10; and (c) continuously feeding the pressurized gas and the mixture of dry powder and pressurized gas from the gas-powder chamber 21 into the delivery channel 10 via the feeding opening 11 until a predetermined amount of the mixture of dry powder and pressurized gas spray out of the emitting opening 12 of the delivery channel for applying onto the internal operation site.

Figure 7:
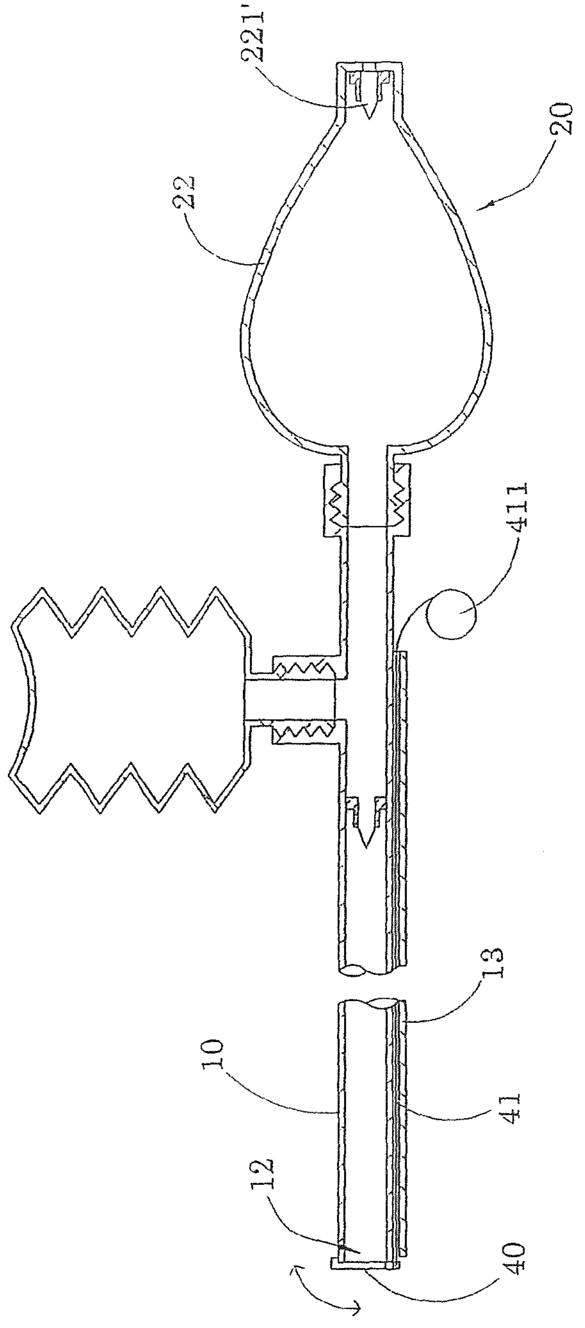
FIG. 7 is a sectional view illustrating an end cap provided at the emitting opening of the delivery channel according to the above preferred embodiment of the present invention.

The gas mentioned above can be any, but preferable medical use clean air, oxygen, or carbon dioxide, or the like. The pressurized gas feeder 22 can be embodied as a manual air pump as shown in FIGS. 1 to 5. The process begins when the air is pumped into the air-powder chamber 21 (either by the manual pump as shown in FIGS. 1-5 or the electrical pump as shown in FIG. 7) mixing with the dry particles of the dry powder. When the present invention is applied for diagnosis and treatment when performing a minimally invasive procedure via endoscope, the mixed dry powder and pressurized air are in turn delivered to an internal wound site through the delivery channel 10 within the working channel of the endoscope. The dry powder finally is spray out to the target tissue or wound site from the emitting opening 12 of the delivery channel 10 under the control and monitoring by physicians via endoscope.

The dry powder used in the present invention refers to dry, smooth and elastic particles. To also ensure a smooth delivery, powder particles should not exceed 400 um; the preferred particle diameter should be between 1 um-250 um. The dry powder used in the present invention can also include nano particles and/or microfiber particles. To ensure a smooth delivery, the average size of the microfiber particles should not exceed 400 um and the preferred particle size should be between 0.01-200 um.

The powder medications used in present invention include, but are not limited to anti-inflammatory drugs (Amoxicillin, Norfloxacin, Gentamicin etc.), anti-ulcer drugs and agents (Omeprazole, Ranitidine, Metronidazole or mucosal protective agent etc.), and anti-neoplastic drugs (Cytotoxic, hormones or biological response modifier).

According to the preferred embodiment of the present invention, powder form Starch-derived Absorbable Polysaccharide Hemostat, SAPH, is used as the dry powder for hemostasis at the internal wound site.

The dry powder used in the present invention also includes, but not limited to, organic or non organic material, chemical substances and compounds, minerals, lipids, polymer, polysaccharide, fiber, proteins, amino acids, polypeptide, and etc.

The dry powder used in the present invention such as nanomaterial and biomaterial include, but not limited to, biocompatible hemostats, surgical adhesives, sealant, anti-adhesion material, enforcement material, fistula closure material, wax, and etc.

Referring to FIGS. 1 to 4, the internal dry powder delivery system of the present invention offers physicians an alternative method to apply dry hemostatic powder to an internal operation site which can be a surgical wound site.

The powder supply device 20 is embodied to comprise a pressurized gas feeder 22 which is an elastic hollow air pump securely connected to a base 23 in a detachable manner, wherein the dry powder 30 is received inside the pressurized gas feeder 22. The dry powder inlet 211 of the gas-powder chamber 21 is detachably connected to the base 23 and communicated with the pressurized gas feeder 22.

Therefore, by compressing the pressurized gas feeder 22, the SAPH particles of dry powder 30 is pressurized to enter the gas-powder chamber 21. When the air pump 22 is compressed, air is pumped in the gas-powder chamber 21 through a gas regulator 24, which is a one-way air valve, and mixes with the dry powder 30 in the air-powder chamber 21. When the manual air pump 22 is released, additional air enters through the gas regulator 24 to prevent negative air pressure within gas-powder chamber 21 to ensure the mixture of dry powder and pressurized air pumping into the delivery channel 10 in a one-way manner without any re-sucking back into the gas-powder chamber 21.

According to the preferred embodiment as shown in FIG. 1, the gas regulator 24 comprises a gas valve 240 provided at a side of the gas-powder chamber 21, which is about 2-5 cm preferably from the base 23 and air communicating with delivery channel 10. A powder filter 241 is provided between the gas-powder chamber 21 and the gas valve 240 to prevent any powder entering the gas valve 240.

The gas valve 240 according to the preferred embodiment as shown in FIG. 1 comprises a hollow housing 242 having an air inletting opening 243, a valve ball 244 disposed inside the housing 242, and a position stopper 245 provided at a bottom inside the housing 242. A diameter of the valve ball 244 is smaller than the diameter of the housing 242 and larger than the inletting opening 243, and that the valve ball 244 can be moved between the inletting opening 243 and the position stopper 245. When the valve ball 244 is pressed to block the inletting opening 243, the gas valve 240 is closed from any air to enter. When the valve ball 244 is dropped to the position stopper 245, the inletting opening 243 is opened to enable air flowing into the powder supply device 20.

Accordingly, when the pressurized gas feeder (air pump) 22 is compressed, a portion of the air pressure produced at the dry powder outlet 212 (i.e. the position between the gas valve 240 and the feeding opening 11 of the delivery channel 10) presses the valve ball 244 radically outwardly to block the inletting opening 243 so as to produce the air pressure in the gas-powder chamber 21 mixing with the dry powder 30 and blow the dry powder 30 into the delivery channel 10 for delivering the mixture of dry powder and pressurized air to the emitting opening 12 of the delivery channel 10 for spraying onto internal operation site.

Once the air pressure is reduced when the compression to the pressurized gas feeder 22 is released, the valve ball 244 drops and returns to the position stopper 245 to reopen the inletting opening 243 so that air can enter the one-way gas valve 240 and supply to the pressurized gas feeder (air pump) 22 to release the negative air pressure therein in order to prevent any re-sucking of the dry powder 30 back to the pressurized gas feeder 22.

Figure 2:
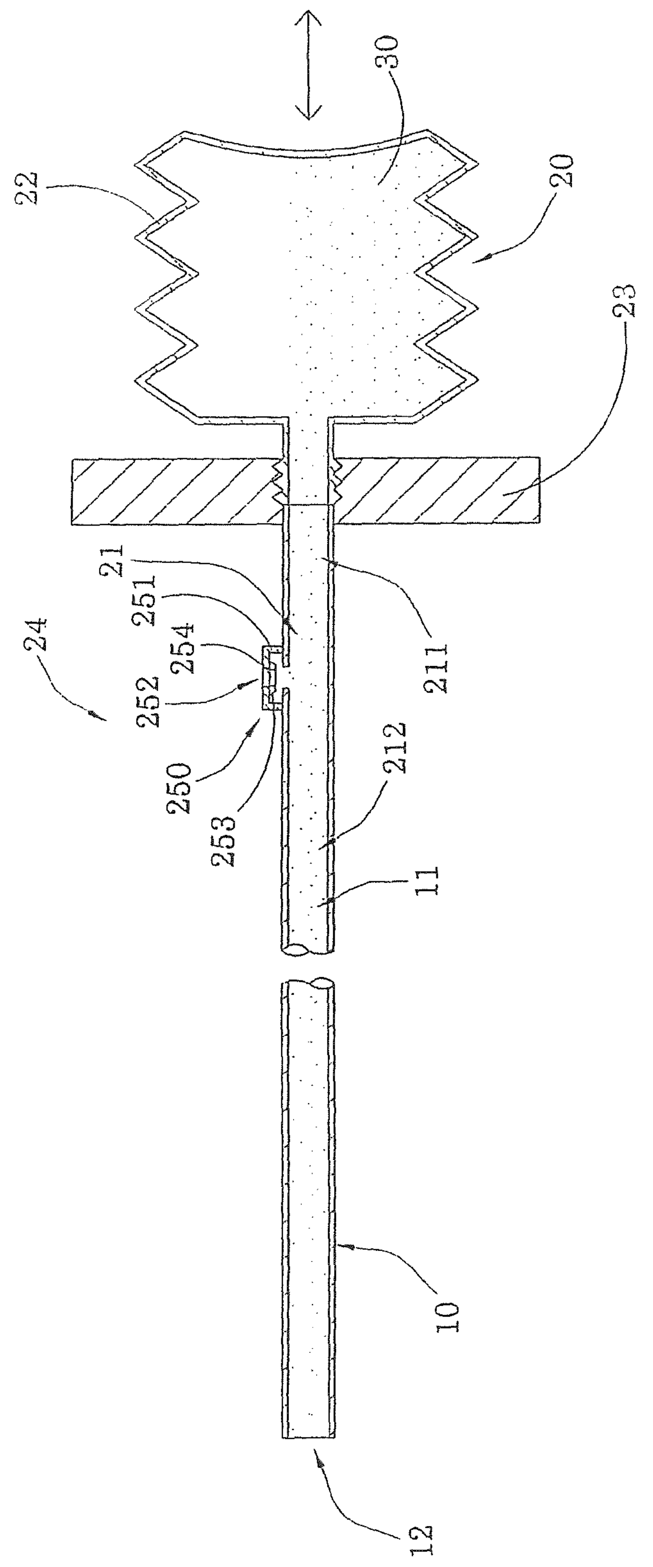
FIG. 2 is a sectional view of the internal dry powder delivery system according to the above preferred embodiment of the present invention, wherein an alternative mode of the gas regulator is illustrated.

Referring to FIG. 2, the gas regulator 24 comprises an alternative gas valve 250 which comprises a housing 251 having an air inletting opening 252, a resilient element 253 disposed within the housing 251, and a blocker 254 affixed to the resilient element 253 and positioned between the inletting opening and the resilient element 253 within the housing 251 for blocking or opening the inletting opening 252.

Accordingly, when the pressurized gas feeder (air pump) 22 is compressed, a portion of the pressurized air produced at the dry powder outlet 212 (i.e. the position between the gas regulator 24 and the feeding opening 11 of the delivery channel 10) presses the blocker 254 outwardly to block the inletting opening 252 so as to produce the air pressure in the gas-powder chamber 21 mixing with the dry powder 30 and blow the dry powder 30 into the delivery channel 10 for delivering the mixture of dry powder and pressurized air to the emitting opening 12 of the delivery channel 10 for spraying onto internal operation site.

Once the air pressure is reduced when the compression to the pressurized gas feeder 22 is released, the blocker 254 is rebound by the resilient element 253 to return to its original position. When the pressurized gas feeder (air pump) 22 is compressed, the ball 263 is pressed by the air pressure produced at the dry powder outlet 212 to move from the front end piece 2611 towards the rear end piece 2612 to open the feeding valve 260 for delivering the mixture of dry powder and pressurized air to the emitting opening 12 of the delivery channel 10 for spraying onto the internal operation site.

Once the air pressure is reduced when the compression to the pressurized gas feeder 22 is released, the ball 263 is rebounded by the spring element 262 to its original position to block the entrance of the front end piece 2611 to close the feeding valve 260.

Figure 3:
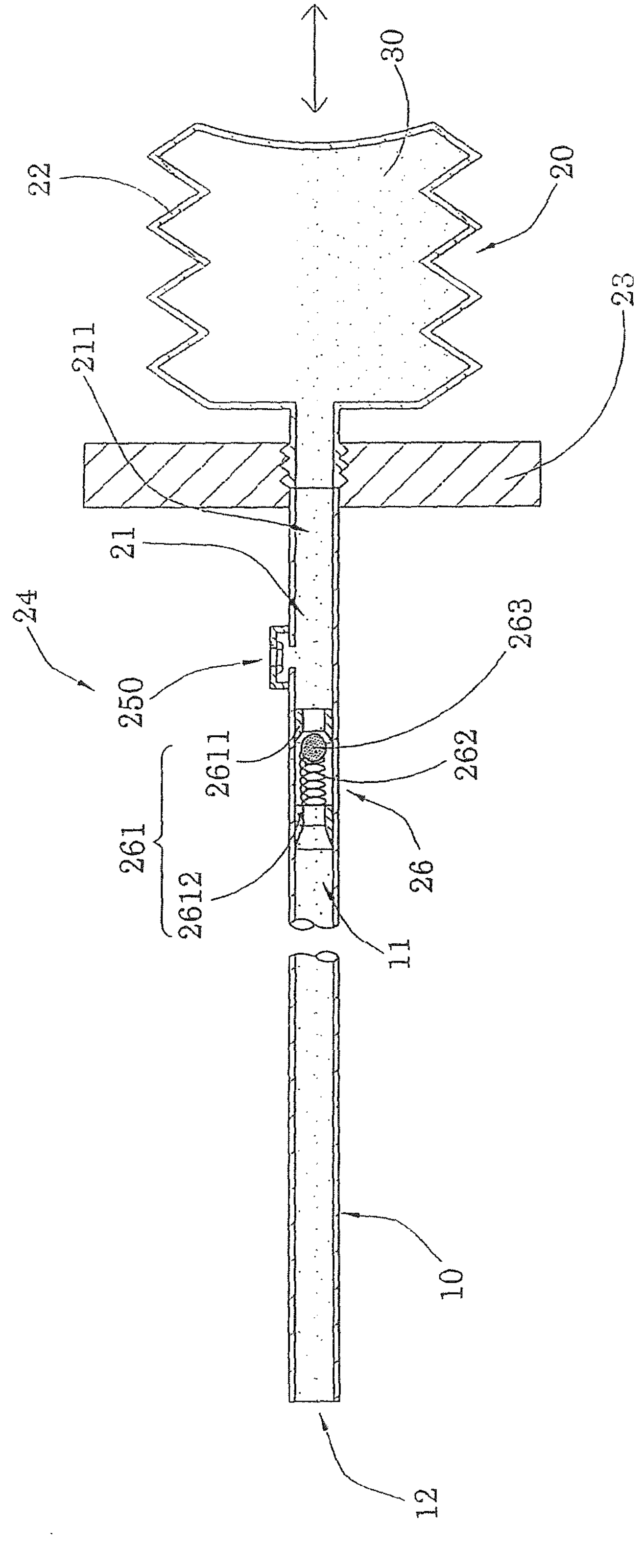
FIG. 3 is a sectional view of the internal dry powder delivery system according to the above preferred embodiment of the present invention, wherein another alternative mode of the gas regulator is illustrated.

Referring to FIG. 3, the gas regulator 24 of the above preferred embodiment as illustrated in FIG. 2 further comprises a one-way feeding valve 260 affixed at the dry powder outlet 212 of the gas-powder chamber 21, positioning right after the gas valve 250. The one-way feeding valve 26 comprises a seat 261 affixed inside the feeding opening 11 having a front end piece 2611 and a rear end piece 2622 defining a chamber therebetween, a spring element 262, and a ball 263 which is attached to a front end of the spring element 262 in such a manner that the ball 263 is able to be moved axially inside the delivery channel 10 between the two end pieces 2611, 2612.

When the pressurized gas feeder (air pump) 22 is compressed, the air pressure produced at the dry powder outlet 212 presses the ball 263 to move from the front end piece 2611 towards the rear end piece 2612 to open the feeding valve 260 for delivering the mixture of dry powder and pressurized air to the emitting opening 12 of the delivery channel 10 for spraying onto the internal operation site.

Also, once the air pressure is reduced when the compression to the pressurized gas feeder 22 is released, the ball 263 is rebound by the spring element 262 to its original position to block the entrance of the front end piece 2611 to close the feeding valve 260.

Figure 4:
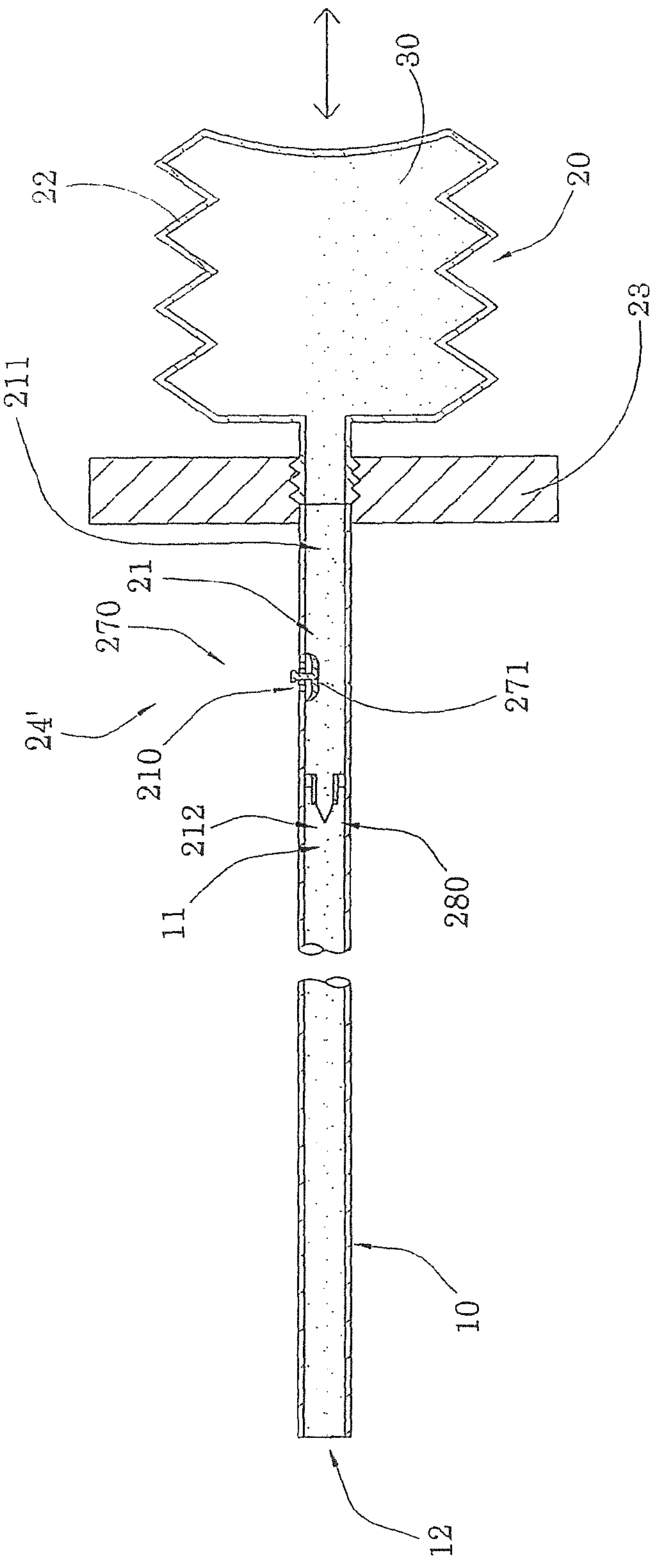
FIG. 4 is a sectional view of the internal dry powder delivery system according to the above preferred embodiment of the present invention, wherein another alternative mode of the gas regulator is illustrated.

Referring to FIG. 4, the gas regulator 24 of the above preferred embodiment as is substituted by an alternative gas regulator 24' which includes an alternative gas valve 270 and an alternative feeding valve 280 to substitute the gas valve 250 and feeding valve 260 respectively. The gas valve 270, which is provided at an air opening 210 formed at a side of the gas-powder chamber 21, comprises a resilient blocking element 271 which is in umbrella shape and disposed in the gas-powder chamber 21 in a movable manner between a blocking position to block the air opening 210 when it is moved towards the air opening 210 and an opening position to unblock the air opening 210 when it is moved away from the air opening 210. The feeding valve 280 is a one-way valve that is normally closed and opens due to pressurized air pushing towards the emitting opening 12.

When the pressurized gas feeder (air pump) 22 is compressed, the air pressure produced at the dry powder outlet 212 presses the resilient blocking element 271 to block the air opening 210 and opens the feeding valve 280 for delivering the mixture of dry powder and pressurized air to the emitting opening 12 of the delivery channel 10 for spraying onto the internal operation site.

Once the air pressure is reduced when the compression to the pressurized gas feeder 22 is released, the feeding valve 280 returns to its close position and the resilient blocking element 271 rebounds to its original position to reopen the air opening 210 so that air can enter the gas valve 270 and supply to the pressurized gas feeder (air pump) 22 to release the negative air pressure therein in order to prevent any re-sucking of the dry powder 30 back to the pressurized gas feeder 22.

According to the preferred embodiment as shown in FIGS. 1 to 4, the pressurized gas feeder 22 is screwed to the base 23 which can be embodied as a hand piece base so that one can unscrew and detach the pressurized gas feeder 22 to refill powder 30 into the empty pressurized gas feeder 22 or filling it with different powder medication. Also, it is appreciated that more than one pressurized gas feeders can be used to selectively communicate with the gas-powder chamber 21 for different applications.

Figure 5:
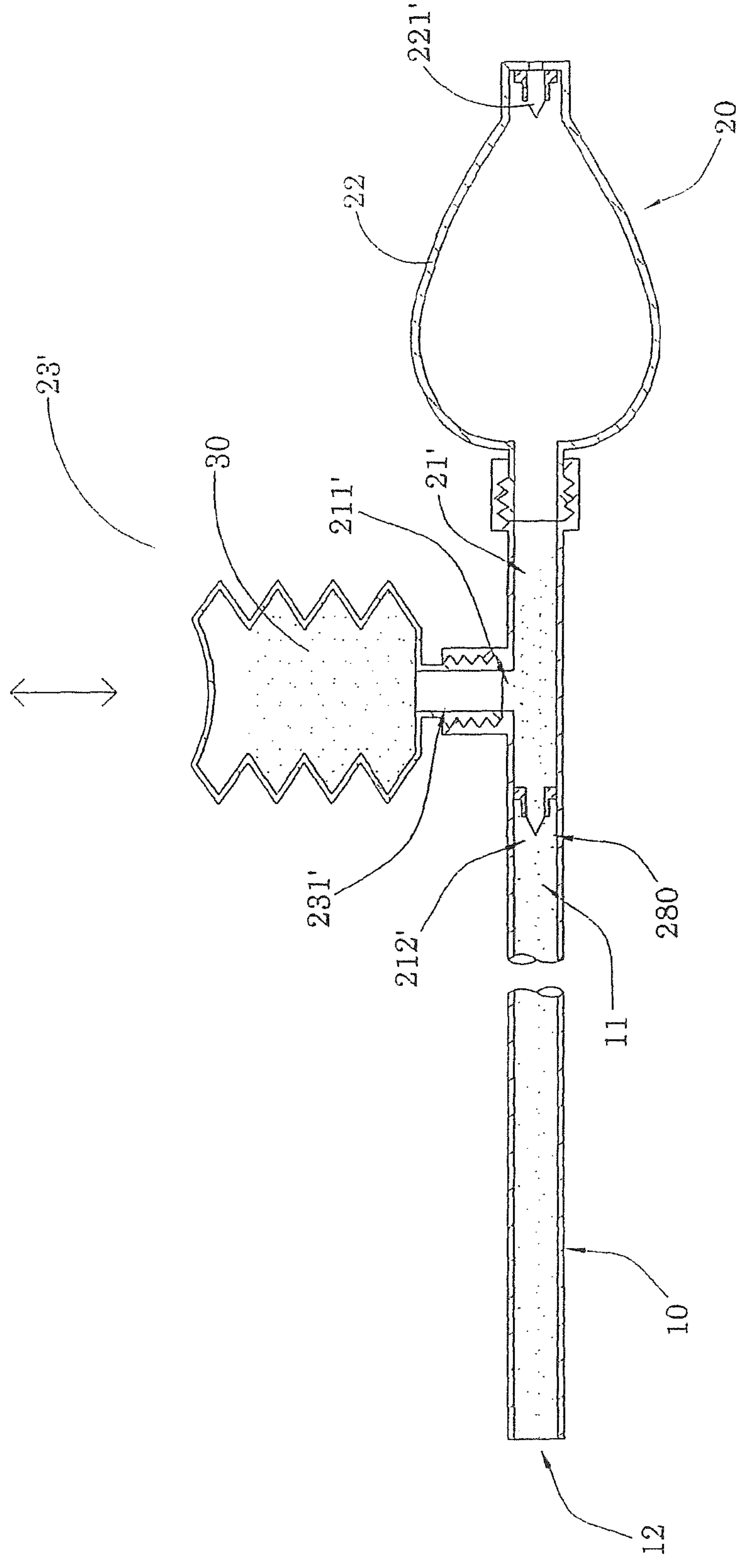
FIG. 5 is a sectional view of the internal dry powder delivery system according to an alternative mode of the above preferred embodiment of the present invention

Referring to FIG. 5, an alternative mode of the powder supply device 20' of the internal dry powder delivery system is illustrated, which is connected to the feeding opening 11 of the delivery channel 10 similar to the above preferred embodiment as shown in FIGS. 1-4. The powder supply device 20' comprises a gas-powder chamber 21' and a pressurized gas feeder 22'.

The gas-powder chamber 21' has dry powder inlet 211' for feeding in a predetermined amount of dry powder therein and a dry powder outlet 212' communicating with the feeding opening 11 of the delivery channel 10.

The pressurized gas feeder 22' produces pressurized gas in the gas-powder chamber 21' mixing with the dry powder therein to form a mixture of dry powder and pressurized gas for blowing into the delivery channel 10 through the feeding opening 11 thereof. Thereby, a continuous feeding of the pressurized gas and the mixture of dry powder and pressurized gas into the delivery channel 10 from the gas-powder chamber 21' substantially renders the mixture of dry powder and pressurized gas to deliver to the emitting opening 12 of the delivery channel 10 and spray onto the designated internal operation site.

The powder supply device 20' further comprises a powder feeder 23' which is seadedly connected to the dry powder inlet 211' provided at a side of the gas-powder chamber 21' in a detachable manner while the exit opening 231' of the powder feeder 23' is communicated with the dry powder inlet 211'. The dry powder 30 is received in the powder feeder 23' and arranged to feed into the gas-powder chamber 21' through the exit opening 231' and the dry powder inlet 211'.

The pressurized gas feeder 22' which is a manual bladder air pump sealedly connected to one end of the gas-powder chamber 21' for pumping pressurized air into the gas-powder chamber 21' manually. The gas regulator 24' comprises a one-way gas valve 221' provided on the pressurized gas feeder 22' and a feeding valve 280' affixed at the dry powder outlet 212' of the gas-powder chamber 21', similar to that as shown in FIG. 4, Accordingly, when the pressurized gas feeder 22' is compressed, the gas valve 221' is closed to block any outside air entering the pressurized gas feeder 22' so as to pump in pressurized air into the gas-powder chamber 21' mixing with the dry powder 30 therein, to open the feeding valve 280' and to blow the dry powder 30 into the delivery channel 10' for delivering the mixture of dry powder and pressurized air to the emitting opening 12 of the delivery channel 10 for spraying onto internal operation site.

Once the air pressure is reduced when the compression to the pressurized gas feeder 22' is released, the feeding valve 280' returns to its close position and the gas valve 221' opens to enable external gas (outside air) entering the pressurized gas feeder 22' to release the negative air pressure therein in order to prevent any re-sucking of the dry powder 30 back to the gas-powder chamber 21' and the pressurized gas feeder 22'.

According to the preferred embodiment, the powder feeder 23' is screwed to the dry powder inlet 211' so that one can unscrew and detach the powder feeder 23' to refill the empty powder feeder 23' or filling it with different powder medication. Also, it is appreciated that more than one powder feeders can be used to selectively communicate with the dry powder inlet 211' for different applications.

Figure 6:
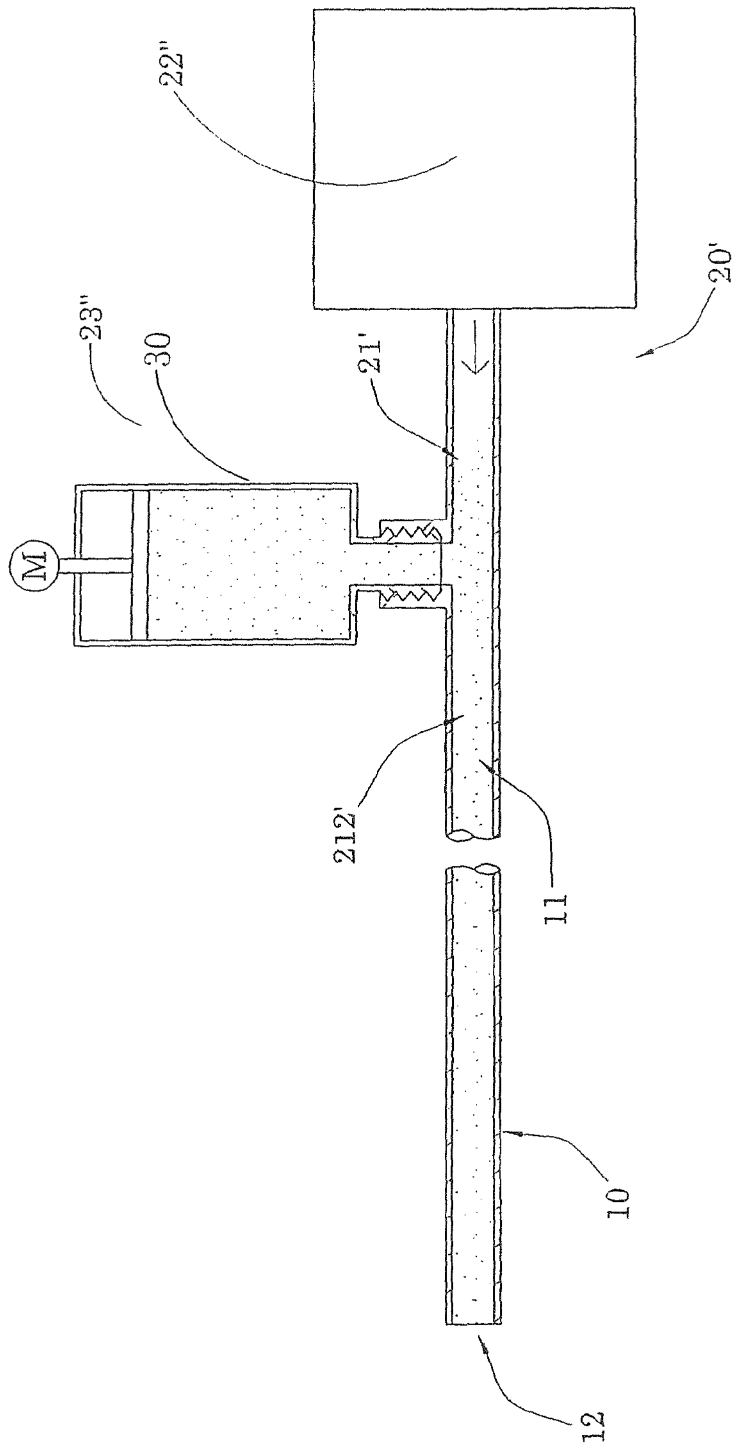
FIG. 6 is a sectional view of the internal powder delivery system according to an alternative mode of the above preferred embodiment of the present invention.

FIG. 6 illustrates an alternative mode of the embodiment as shown in FIG. 5, wherein the powder feeder 23' is substituted by a powered powder feeder 23" to automatically feeding in dry powder 30 into the gas-powder chamber 21' and the pressurized gas feeder 22' is also substituted by an electrical pressurized gas feeder 22" which is an electrical air pump to automatically and continuously produce positive pressurized air into the gas-powder chamber 21'. Since both the powder feeder 23" and the pressurized gas feeder 22" are automate devices, processor can be used to provide electronic control of the powder feeder 23" to equipped with the pressurized gas feeder 22" to ensure continuous and smooth feeding of the mixture of dry powder and pressurized gas to the delivery channel 10 and spraying onto the designated internal operation site.

It is worth mentioning that more than one powder feeders 23' or 23" can be used to connect to the gas-powder chamber 21, 21' which are selectively switched to equip with the pressurized gas feeder 22', 22" to feeding dry powder through the delivery channel 10. Also, a catheter can be used and functioned as the delivery channel 10.

Referring to FIG. 7, the internal dry powder delivery system of the present invention as embodied and disclosed in FIGS. 1 to 6 may further comprises an end cap 40 which is arranged to normally cover the emitting opening 12 and be removed to open the emitting opening 12 for spraying the dry powder 30 onto the internal operation site. According to the preferred embodiment, the delivery channel 10 further comprises an additional operation channel 13 along the length of the delivery channel 10 and an operation cable 41 having one end connected to the end cap 40 and another end extended through the operation channel 13 to connect with a handle 411. The end cap 40 remains covering the emitting opening 12 to prevent any body fluid such as blood, gastric juice, and etc., entering the emitting opening 12 while inserting and extending the delivery channel 10 inside the human or animal body to the designated internal operation (tissue/organ) site. When the emitting opening 12 reaches a position adjacent to the designated internal operation site, the user can simply operate the handle 411 to pull the operation cable 41 to pivotally move the end cap 40 away from the emitting opening 12 to open it so as to enabling the mixture of dry powder and pressurized gas to be pumped to spray onto the designated internal operation (tissue/organ) site.

Alternatively, the end cap 40 can be detachably attached to the distal end of the delivery channel 10 to cover the emitting opening 12. After the delivery channel 10 is inserted into the beings until the emitting opening 12 reaches a position adjacent to the internal operation site and the mixture of dry powder and pressurized gas is deliver to the emitting opening 12, the pressure of the pressurized gas is capable of pushing the end cap 40 to detach from distal end and open the emitting opening 12.

In view of above, the pressurized gas feeder of the present invention can selectively use one of following types of air pressure source:

1. By connecting to the manual air pump 22 as shown in FIGS. 1 to 5, physicians can either continuously or sporadically control the amount of air/powder released into the gas-powder chamber 21, 21'. The gas valves of the hand pump can prevent powder/air reflux, which ensure one-way delivery to the designated internal operation site. Manual air pump gives physicians simple control over the amount of powder and air entering the delivery channel 10.

2. Using the electrical pump as shown in FIG. 6 offers a more consistent flow of gas or air. The gas or air released from the electrical pump will enter the gas-powder chamber 21, 21', mix with the dry powder particles and go through the connected delivery channel 10. Gas valve is installed in the device to prevent air/powder reflux.

3. The device could be connected to medical-use oxygen, carbon dioxide, and other medical use clean-air to offer a continuously flow of gas and limit the possibility of powder and tip occlusion in the delivery channel 10. The gas supply to be used can be directly fed to the inletting opening 243 of the gas valve 240 as shown in FIG. 1, the inletting opening 252 of the gas valve 250 as shown in FIGS. 2 and 3, the air opening 210 as shown in FIG. 4, and the gas valve 221' as shown in FIG. 5.

Figure 8:
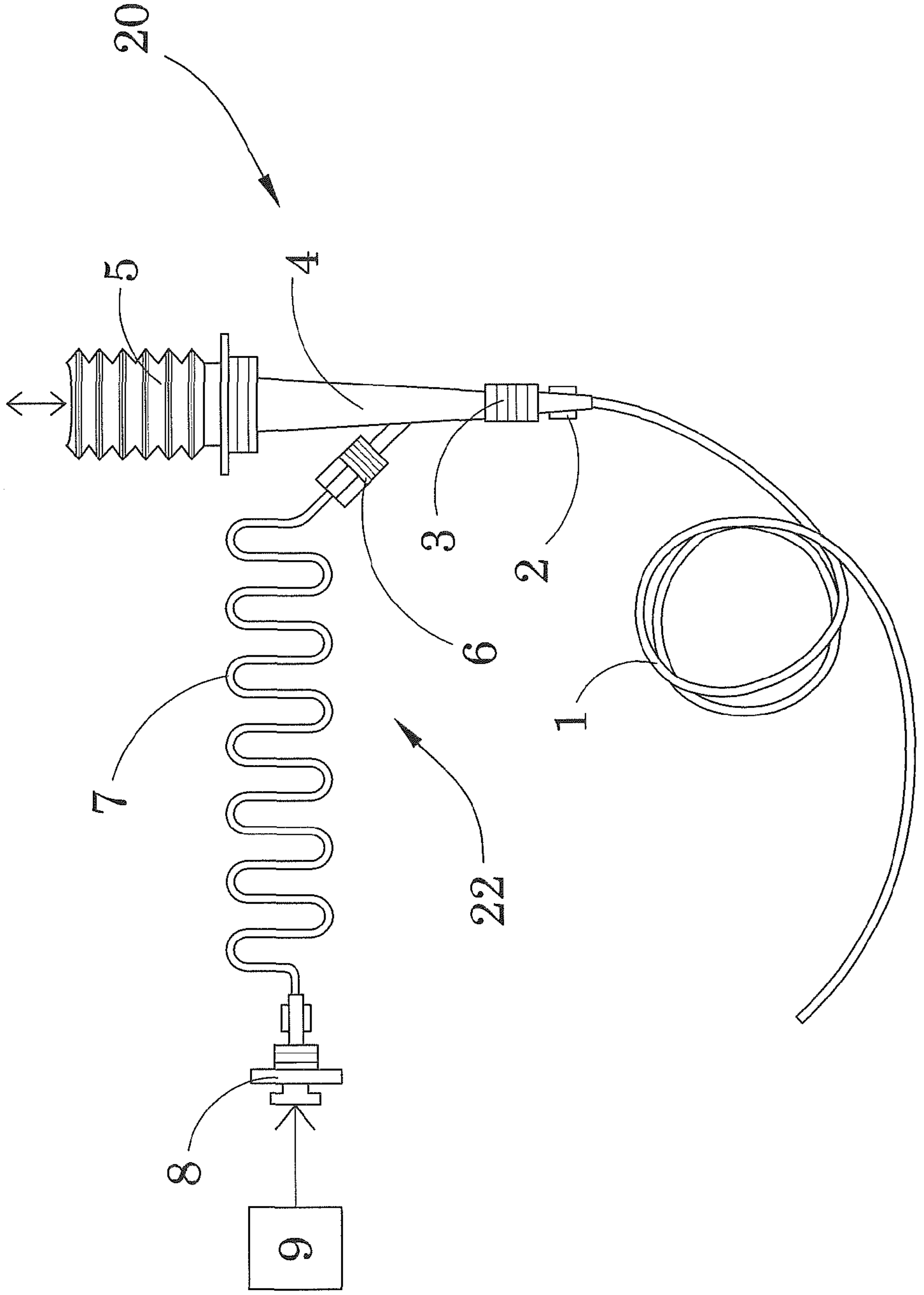
FIG. 8 is a schematic view of an internal powder delivery system, which is embodied as a one way delivery system of hemostat powder during surgery, according to another alternative mode of the above preferred embodiment of the present invention.

Referring to FIG. 8, an one way delivery system of hemostat powder during surgery according to an alternative mode of the preferred embodiment of the present invention is illustrated, wherein the elongated tubular delivery channel 10 comprises a powder delivery catheter 1 having a feeding opening at one end thereof and an emitting opening at a distal end thereof (i.e. the catheter tip), female luers 2 and male luer locks 3 provided at the feeding opening of the powder delivery catheter 1.

The powder supply device 20 comprises a gas powder mixer 4 providing a gas powder mixing chamber and a powder dispenser (bellow) 5 which is screwed to the gas powder mixer 4 and communicated with the gas powder mixing chamber therein. The hemostat powder is filled in the powder dispenser (bellow) 5 and is adapted to be delivered via the powder delivery catheter 1 to the site of bleeding. The pressurized gas feeder 22 of the powder supply device 20 further comprises a male luer lock 6, a gas delivery tube 7 having one end connected with the gas powder mixer 4 and communicating with the gas powder mixing chamber therein via the male luer lock 6, a female luer 8 which is connected to another end of the gas delivery tube 7 and an external gas source 9.

During operation, the external gas source (pump) 9 is switched on first to produce an airflow of 3 L/min, which is embodied as a 'maintaining gas flow'. Insert the powder delivery catheter 1 through an endoscope working channel to a designated bleeding site. The maintaining gas flow is pumped through the gas delivery tube 7, the gas powder mixing chamber 4 and the powder delivery catheter 1 to prevent reflux of gas and fluid into the powder delivery catheter 1 from the gastrointestinal tract during insertion of the powder delivery catheter 1 into the endoscope. Then, pump the powder dispenser 5 as a 'working gas flow' to deliver the powder to the designated bleeding site through the powder delivery catheter 1 to emit via the emitting opening thereof.

According to the alternative mode as shown in FIG. 8, to prevent from powder occlusion in the powder delivery catheter 1 while inserting the powder delivery catheter 1 into the endoscope working channel to its designated position, a special feature of 'dual gas channels' is provided. One of the gas channels provides the 'maintaining gas flow' to ensure that the pressure inside the powder delivery catheter 1 is higher than the pressure inside the gastrointestinal tract or the thoracic/abdominal cavity where the catheter tip is located. This prevents gas reflux from the gastrointestinal tract or thoracic/abdominal cavity into the powder delivery catheter 1 which may result in powder occlusion therein. The 'working gas flow' on the other hand delivers the dry powder to the designated site through the powder delivery catheter 1.

Figure 9:
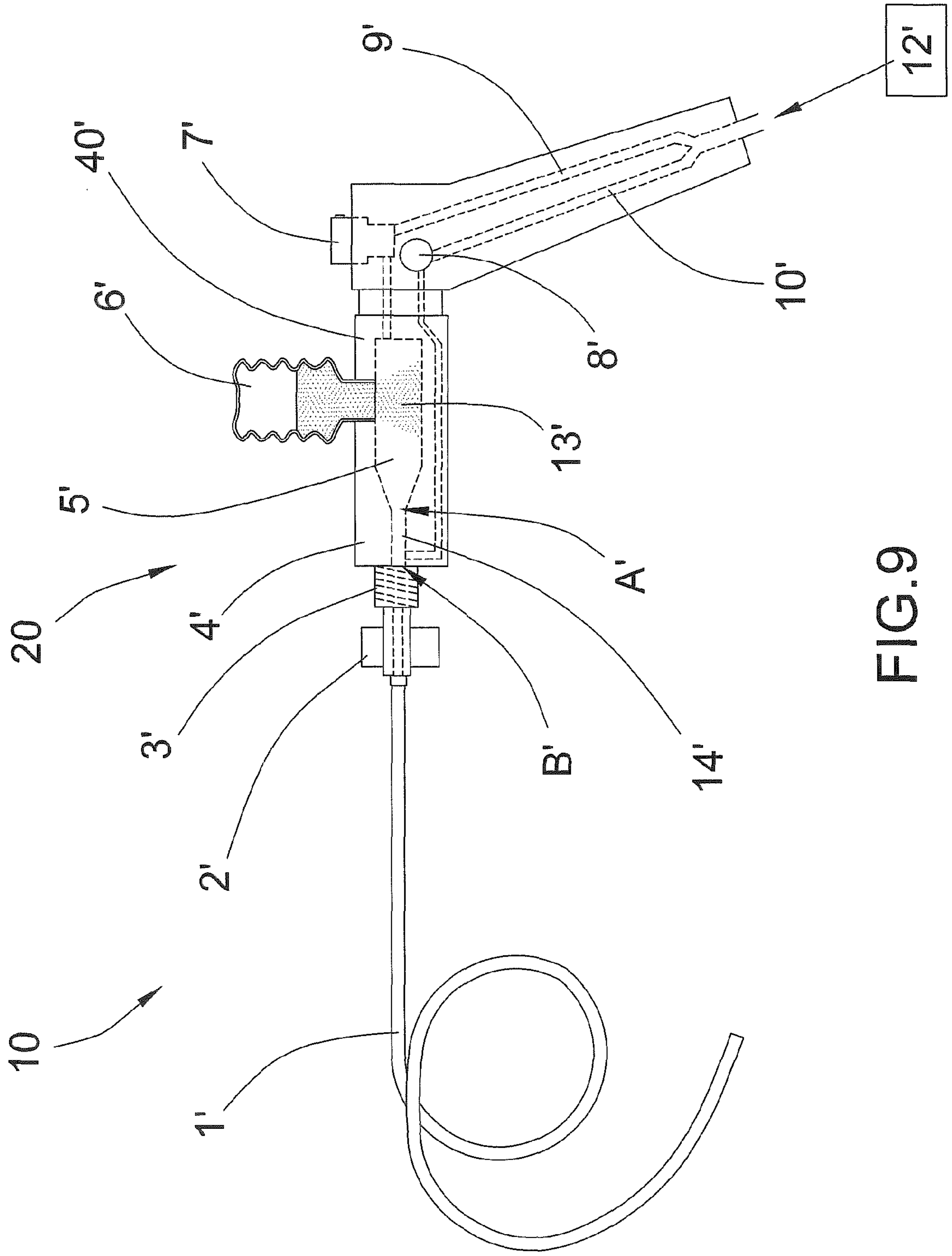
FIG. 9 is a schematic view illustrating an alternative mode of the internal powder delivery system in FIG. 8 according to the present invention.

FIG. 9 illustrates an alternative advance mode of the powder delivery system as shown in FIG. 8, wherein the elongated tubular delivery channel 10 also comprises a powder delivery catheter 1' having a feeding opening at one end thereof and an emitting opening at a distal end thereof (i.e. the catheter tip), female luers 2' and male luer locks 3', wherein the female luers 2' and the male luer locks 3' are provided at the feeding opening of the powder delivery catheter 1'.

The powder supply device 20 comprises a gas powder mixer 4' providing a gas powder mixing chamber 5' therein and a powder dispenser 6' which is screwed on top of the gas powder mixer 4' and filled with hemostat powder 13'. The gas powder mixing chamber 5' has an inlet end and an outlet end connecting and communicating with the feeding opening of the powder delivery catheter 1' via a connecting channel 14'. The end where the connecting channel 14' connecting the outlet end of the gas powder mixing chamber 5' is defined as a connection point A. The powder delivery catheter 1' is inserted through the endoscope working channel to reach the bleeding site. The powder delivery system further comprises a working gas flow switch 7' and a maintaining gas flow switch 8' provided at the gas powder mixer 4'.

According to this alternative advance mode, the gas powder mixer 4' further comprises a hand piece 40' integrally connected thereto, where the working gas flow switch 7' and the maintaining gas flow switch 8' are installed to the hand piece 40' for ease of operation. The hand piece 40' has a working gas flow channel 9' and a maintaining gas flow channel 10' extended therein, wherein one end of each of the working gas flow channel 9' and the maintaining gas flow channel 10' are joined for connecting to an external gas source 12' while another end of the working gas flow channel 9' is extended and connected to the inlet end of the gas powder mixing chamber 5' and another end of the maintaining gas flow channel 10' is extended and connected to the connecting channel 14' at a connection point B.

The external gas source 12' supplies pressurized gas to flow through the working gas flow channel 9' as working gas flow to enter into the gas powder mixing chamber 5' and to flow through the maintaining gas flow channel 10' as maintaining gas flow to a position between the feeding opening of the powder delivery catheter 1' and the outlet end of the gas powder mixing chamber 5'. The working gas flow switch 7' is provided at a positioned along the working gas flow channel 9' for controlling the supply of the gas flow therethrough and the maintaining gas flow switch 8' is provided at a position along the maintaining gas flow channel 10' for controlling the supply of gas flow therethrough.

During operation, the maintaining gas flow can be adjusted via the maintaining gas flow switch 8' to a pressure higher than the pressure in the gastrointestinal tract where the catheter tip is located. The powder delivery catheter 1' is inserted through the endoscope working channel to the designated bleeding site. The maintaining gas flow is pumped through the maintaining gas flow channel 10' all the way to the feeding end of the powder delivery catheter 1' to prevent reflux of gas and powder in the powder delivery catheter 1' while the working gas flow remains closed at this point via the working gas flow switch 7'. Open the working gas flow switch 7' at the hand piece 40'. The working gas flow will enter the gas powder mixing chamber 5' and push the powder in the gas powder mixing chamber 5' forward into the powder delivery catheter 1'.

As shown in FIG. 9, the maintaining gas flow channel 10' in the gas powder mixer 4' is separated from the gas powder mixing chamber 5'. To ensure the working mechanism of the dual gas channel configuration according to the present invention, the connection point B of the maintaining gas flow channel 10' to the powder delivery catheter 1' must be located closer to the male luer locks 3' than the connection point A of the gas powder mixing chamber 5' with the powder delivery catheter 1' so as to allow the maintaining gas flow to bypass the gas powder mixing chamber 5' while the working gas flow maintaining an unobstructed delivery passage for the powder.

In view of above, besides the options for various air/gas sources, the present invention offers two types of air-powder chambers to provide a tailor-made apparatus via endoscope for any minimally invasive procedures both for diagnosis and treatments.

The first option offers the three-way air-powder chamber with an external gas source, a powder feeder, a pressurized gas feeder, and a delivery channel (catheter) attached to the gas powder chamber. The main body of the gas powder chamber has two incoming openings, for both gas and the dry powder, and a dry powder outlet connected to the catheter. The incoming gas flow will mix with the dry powder released from the powder feeder and then delivered through the catheter of the working channel via endoscope.

The second option provides a two-way air-powder chamber; it only has an incoming and outgoing opening. It differs with the previous device by eliminating the external powder feeder since the main mixing chamber is pre-filled with the dry powder. Once the gas is released, it mixes with the dry powder and the mixture is delivered through catheter of the working channel via endoscope. It is preferably for portable and disposable usage due to its compact size and simplified structure.

The delivery channel 10 (powder delivery catheter 1, 1') will preferably used with medical-use materials such as PE and TEF. It is essential to select a material that has the strength and the flexibility to be inserted into the working channel of endoscope and endure any folding or twisting which could cause congestion. For gastro-intestinal endoscope, the diameter of the delivery channel 10 is preferably smaller than the regular working channel's diameter of the endoscope being used. Currently, the standard working channel diameters of gastro and intestinal endoscope are about 2.8 mm and 3.2 mm respectively. The length of the delivery channel 10 (powder delivery catheter 1, 1') should be longer than the total length of the endoscope which it is inserted into. Normally, the average total length of gastro and intestinal endoscope are about 1600 mm and 2300 mm respectively.

Besides the incoming gas source and the outgoing channel, all connecting outlets of the system should remain completely sealed throughout use to minimize air/powder reflux and tip occlusion.

It is worth mentioning that the pressure of gas should be maintained higher enough to overcome the resistance of particles with particles, particles with the systems, plus the pressure inside of gastro-intestine where the catheter tip located.

The internal dry powder delivery system of the present invention differentiates itself from conventional medication delivery method in its specification for the delivery of dry powder particles via the working channel of an endoscope. For example, prior art patent, WO2006/049463A1, focuses on liquid and gel-form medication delivery. Liquid's fluidity causes minimal obstruction in the working channel of the endoscope, which does not contain the same strategy and technology as a dry powder delivery service via endoscope.

The current endoscope invention includes both gastro and intestinal endoscopes. It can be also adapted in laparoscope, thoracoscope, hysteroscope, cytoscope, laryngoscope, and nasopharyngoscope. The working channel diameter of laparoscope, thoracoscope, hysteroscope, cytoscope and laryngoscope are normally much bigger than gastro-intestinal endoscope. So the challenges will be less for physicians to deliver the powder format drug to the wound sites via laparscope, thoracoscope, hysteroscope, cytoscope and laryngoscope The working channel mentioned above is the irrigation channel or a biopsy clamp channel in the endoscopic cannula.

The present invention offers a new powder format drug delivery method for physicians via endoscope. It could be used with various purposes such as hemostatic, antibiotic, tissue repair, mucosal protection, ulcer repair and antineoplastic treatment, etc.

The present invention offers a new technique for physicians to use an endoscope to access the abdominal cavity, thoracic cavity and pelvic cavity via natural orifices to directly apply powdered medication to the internal target tissue/organs for the purpose of hemostasis, anti-inflammatory, anti-adhesion, tissue repair, congenital defect tissue repair, fistula closure, topical and localized chemotherapy/radiotherapy for tumor treatment, and etc. By using the internal dry powder delivery system of the present invention, physicians can directly apply the biocompatable polysaccharide hemostatic powder to the bleeding sites via endoscope during invasive surgery to achieve hemostasis.

When all components (pressurized gas feeder, gas-powder chamber, and working delivery channel) are assembled, the present invention can provide a complete and new applicator via endoscope. The manual air pump and powder feeder allow physicians to control the flow of air and the amount of powder released through the delivery channel. The gas and feeding valves provided to the gas-powder chamber will eliminate air/powder reflux. The mechanism of this system begins with the release of gas by a manual or electrical air pump, which mixes with the dry powder presented in the air-powder chamber. By compressing the pressurized gas feeder and/or the dry powder feeder, physicians can easily control the amount of gas/powder mixture released into the delivery channel. The gas flow continues to push the mixture throughout the entire delivery channel, overcoming any obstructions presented by the channel wall and/or between particles.

By using the internal dry powder delivery system of as suggested in the present invention, physicians can directly apply the powder-format biocompatible adhesives to the wound site in the gastro-intestinal wall via endoscope by minimal invasive surgery to achieve hemostasis and sealant treatment.

By using the internal dry powder delivery system as disclosed in the present invention, physicians can directly apply the antibiotic powder to the infection site in the gastro-intestinal wall via endoscope by minimal invasive surgery to achieve anti-infection treatment.

By using the internal dry powder delivery system as disclosed in the present invention, physicians can directly apply the anti-ulcer powder form medication to the ulcer site in the gastro-intestinal wall via endoscope by minimal invasive surgery to achieve anti-ulcer treatment.

By using the internal dry powder delivery system as disclosed in the present invention, physicians can directly apply the anti-cancer/tumor powder form medication to the cancer/tumor site in the gastro-intestinal wall via endoscope by minimal invasive surgery to achieve antineoplastic treatment.

By using the internal dry powder delivery system as disclosed in the present invention, physicians can directly apply the illustrating agent to the cancer/tumor site in the gastro-intestinal wall.

By using the internal dry powder delivery system as disclosed in the present invention, physicians can access internal organs in the abdominal, thoracic and pelvic cavities using an endoscope inserted through natural orifices to directly deliver medications to the target tissue/organ via the working channel of the endoscope for the purpose of hemostasis, anti-inflammatory, anti-adhesion, tissue repair, congenital defect tissue repair, perforation repair, fistula closure, promote wound healing, topical and localized chemotherapy/radiotherapy for tumor treatment etc. These dry powder materials include, but not limited to, biocompatible hemostats, adhesives, surgical sealants, anti-adhesion materials, tissue enforcement materials, fistula closure materials, wax, and etc.

By using the internal dry powder delivery system and method thereof as disclosed in the present invention, physicians can apply anti-inflammatory medications, immunosuppressive medication, nutrient powder (including trace elements, protein and amino acids), vaccines and other anti-microbial drugs directly into the digestive tract. In particular, it can be used in the treatment for chronic colitis, malnutrition, parasitic diseases, and etc.

The internal dry powder delivery system and method thereof as disclosed in the present invention can be specifically designed for examination, diagnosis and treatments practices in humans and mammals. It could also be used in forensic science such as autopsy, anatomy research and scientific experiments. Besides medical and scientific uses, the internal dry powder delivery system of the present invention can be applied in engineering, military affairs, navigation, and aviation.

The internal dry powder delivery system and method thereof as disclosed in the present invention can be specifically designed for examination, diagnosis and treatments practices in humans and mammals.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of delivering dry powder to an internal operation site of beings, comprising the steps of:

(a) extending a distal end of an elongated tubular delivery channel to a position that an emitting opening of said delivery channel is adjacent to said internal operation site;

(b) generating a working gas flow containing pressurized gas to mix with dry powder to deliver a mixture of dry powder and pressurized gas to said delivery channel until a predetermined amount of said mixture of dry powder and pressurized gas sprays out from said emitting opening of said delivery channel for application onto said internal operation site;

(c) generating a maintaining gas flow to said delivery channel for preventing gas reflux of said delivery channel so as to prevent reflux of gas and fluid into said delivery channel, wherein said pressurized gas is mixed with said dry powder in a gas powder chamber to deliver said mixture of dry powder and pressurized gas from said gas powder chamber into said delivery channel, wherein an outlet of said gas powder chamber is communicatively linked to said delivery channel; and (d) bypassing said maintaining gas flow to said gas powder chamber, such that said maintaining gas flow does not pass through said gas powder chamber.

2. The method, as recited in claim 1, further comprising the steps of:

(e) configuring a working gas flow channel to communicate with an inlet of said gas powder chamber to guide said working gas flow thereinto; and (f) configuring a maintaining gas flow channel to communicate with a connecting channel, which connects and communicates said outlet of said gas powder chamber with said delivery channel, to guide said maintaining gas flow to said delivery channel.

3. The method, as recited in claim 2, wherein said working gas flow channel and said maintaining gas flow channel are connected to a single gas supplying source.

4. The method, as recited in claim 2, wherein the step (c) further comprises the steps of controlling a supply of said working gas flow to said gas powder chamber via a working gas flow switch, and controlling a supply of said maintaining gas flow to said delivery channel via a maintaining gas flow switch.

5. The method, as recited in claim 1, wherein the step (c) further comprises the steps of controlling a supply of said working gas flow to said gas powder chamber via a working gas flow switch, and controlling a supply of said maintaining gas flow to said delivery channel via a maintaining gas flow switch.

6. The method, as recited in claim 5, wherein said working gas flow switch is connected at said working gas flow channel and said maintaining gas flow switch is connected at said maintaining gas flow channel.

7. The method, as recited in claim 1, wherein said maintaining gas flow is generated to reach said internal operation site before said working gas flow is generated to deliver said mixture of dry powder and pressurized gas at said internal operation site.

8. A method of delivering dry powder to an internal operation site of beings, comprising the steps of:

(a) extending a distal end of an elongated tubular delivery channel to a position such that an emitting opening of said delivery channel is adjacent to said internal operation site;

(b) generating a flow of pressurized gas and dividing said pressurized gas into a working gas flow and a maintaining flow, the working gas flow provided to mix with dry powder in a gas powder chamber to deliver a mixture of dry powder and pressurized gas to said delivery channel until a predetermined amount of said mixture of dry powder and pressurized gas sprays out from said emitting opening of said delivery channel for application onto said internal operation site, wherein said working gas flow and said maintaining gas flow are generated from a single gas supplying source;

(c) preventing reflux of gas and fluid into said delivery channel by said maintaining gas flow generated to said delivery channel; and (d) bypassing said maintaining gas flow to said gas powder chamber, such that said maintaining gas flow does not pass through said gas powder chamber.

9. The method, as recited in claim 8, further comprising the steps of:

(e) configuring a working gas flow channel to communicate with an inlet of said gas powder chamber to guide said working gas flow thereinto; and (f) configuring a maintaining gas flow channel to communicate with a connecting channel, which connects and communicates said outlet of said gas powder chamber with said delivery channel, to guide said maintaining gas flow to said delivery channel.

10. The method, as recited in claim 9, wherein said working gas flow channel and said maintaining gas flow channel are connected to said single gas supplying source.

* * * * *